United States Patent
Hart et al.

(10) Patent No.: US 6,342,692 B1
(45) Date of Patent: Jan. 29, 2002

(54) THERMAL DEVICE FOR MAINTAINING THE TEMPERATURE OF BODY EXTREMITIES

(75) Inventors: Robert D. Hart, Red Lodge; Anita A. Perkins, Anaconda, both of MT (US)

(73) Assignee: Crazy Creek Products, Red Lodge, MT (US)

(*) Notice: Subject to any disclaimer, the term of this patent is extended or adjusted under 35 U.S.C. 154(b) by 0 days.

(21) Appl. No.: 09/587,951

(22) Filed: Jun. 6, 2000

(51) Int. Cl.[7] .................................................. H05B 3/34
(52) U.S. Cl. ........................ 219/528; 219/544; 607/109; 607/114
(58) Field of Search .............................. 219/211, 212, 219/217, 527, 528, 529, 544, 545, 549; 607/108, 109, 110, 111, 112, 114; 602/2, 14; 604/291

(56) References Cited

U.S. PATENT DOCUMENTS

| | | | | |
|---|---|---|---|---|
| 2,590,212 A | * | 3/1952 | Samuels | 219/527 |
| 3,980,070 A | * | 9/1976 | Krupa | 607/114 |
| 4,042,803 A | * | 8/1977 | Bickford | 219/211 |
| 4,326,533 A | * | 4/1982 | Henderson | 607/112 |
| 4,736,088 A | * | 4/1988 | Bart | 219/211 |
| 4,810,859 A | * | 3/1989 | Anabtawi et al. | 219/528 |
| 5,000,176 A | * | 3/1991 | Daniel | 607/108 |
| 5,165,402 A | * | 11/1992 | McCoy | 607/108 |
| 5,188,103 A | * | 2/1993 | Smith | 607/109 |
| 5,247,928 A | * | 9/1993 | Stilts, Jr. | 607/109 |
| 5,395,400 A | * | 3/1995 | Stafford et al. | 607/109 |
| 5,436,429 A | * | 7/1995 | Cline | 219/528 |
| 5,716,388 A | * | 2/1998 | Petelle | 607/108 |
| 5,932,129 A | * | 8/1999 | Hyatt | 219/528 |
| 5,973,302 A | * | 10/1999 | Petrosino | 219/527 |
| 5,974,820 A | * | 11/1999 | Boyd | 219/529 |

* cited by examiner

Primary Examiner—Teresa Walberg
Assistant Examiner—Fadi H. Dahbour

(57) ABSTRACT

A thermal device for maintaining the temperature of body extremities is provided. The device includes a pocket adapted to receive a heating element and a strap attached to the pocket such that the device is adapted to encircle and be secured around a portion of the human body. The pocket has a tri-fold configuration formed from a rear panel, a front panel, and an intermediate panel positioned atop one another, the intermediate panel being positioned between the front panel and the rear panel. Each of the three panels is connected along their respective vertical side edges. The first horizontal edges of the front panel and the rear panel are fixedly attached forming a first open space between the front panel and the intermediate panel and the second horizontal edges of the rear panel and the intermediate panel are fixedly attached forming a second open space therebetween. In operation, a heating element is inserted into the first open space and maneuvered around the first horizontal edge of the intermediate panel until it rests within the second open space of the pocket between the rear and intermediate panels. The device is then placed on the user with the rear panel of the pocket positioned on the interior surface of the wrist and secured in place with the strap.

13 Claims, 1 Drawing Sheet

THERMAL DEVICE FOR MAINTAINING THE TEMPERATURE OF BODY EXTREMITIES

FIELD OF INVENTION

This invention relates to a thermal device for maintaining the temperature of body extremities. More specifically, this invention relates to a device for supplying heat to targeted regions of the human body to prevent the constriction of blood vessels in those regions in cold temperature conditions.

BACKGROUND OF THE INVENTION

Numerous outdoor activities, both occupational and leisurely, require manual dexterity. While the ambient temperature generally presents little problem in warm weather, as the outdoor temperature decreases, the temperature of body extremities also decreases making the effective manipulation of the hands and feet increasingly difficult. Impaired agility may be simply a minor annoyance to one trying to enjoy recreational activity, but it can present a serious safety hazard to one working, for example, with heavy machinery or electrical lines and equipment. Similarly, the safety of extreme athletes that climb mountains, for example, in temperatures often well below the freezing point, is jeopardized when they cannot effectively utilize their extremities.

Various paraphernalia, such as gloves, mittens, insulated socks and the like, is available to increase or maintain the temperature of the hands and feet in cold conditions. While effective for their intended purpose, these items often are bulky and cumbersome. Even in the best case scenario (e.g., a thin, insulated mitten or sock), there is an impediment to the wearer's sense of touch which may present substantial safety hazards in itself. Accordingly, finding an alternative for warming or maintaining the temperature of the hands and feet without the use of such protective coverings has been an on-going challenge for those who spend much of their time out of doors. One alternative that has shown much promise is thermal regulation of the blood and blood vessels flowing into the body extremities.

Constriction of the blood vessels (i.e., a decrease in the diameter of the vessels) is a natural human response when portions of the anatomy are exposed to temperatures cooler than the temperature of the body. Constricted blood vessels naturally carry less blood through them. If the constricted vessels flow into the extremities, the decrease in blood flow to the extremity leads to a corresponding decrease in the temperature of the extremity. Therefore, if constriction of the blood vessels in cold temperature conditions can be minimized, the temperature of the extremity into which the blood vessels flow can be maintained at a more constant level. This is the goal of thermal regulation.

Thermal regulation is simply regulating the temperature of a region of the body through the use of heat or cold. Certain regions of the body are known to respond particularly well to this type of stimulus. For example, regions of the body in which the blood vessels are located close to the skin surface respond particularly well to thermal treatment. The application of heat to these temperature responsive regions decreases constriction of the blood vessels in those regions, even in cold temperature conditions. If the vessels are not constricted but instead remain in a more dilated state, the amount of blood flowing through them stays more consistent. A blood flow which remains relatively consistent will maintain the temperature of the extremity through which it is flowing virtually at a constant level.

The radial and ulnar arteries are the primary source of blood flow to the hands. These arteries, or the larger arteries which supply them with blood, run continuously from the heart to the hands. At the wrist, just prior to entering the hand region, the vessels emerge and run relatively close to the surface of the skin making the wrist a thermally responsive region for maintaining the temperature of the hands. Accordingly, heat applied to the skin at the wrist will effectively decrease constriction of the radial and ulnar arteries. Allowing the radial and ulnar arteries to remain in a more dilated state aids in maintaining the hands at a temperature more closely approximating normal body temperature, even in cold ambient conditions. This allows for more consistent dexterity of the hands.

In order to effectively utilize thermal regulation in lieu of protective hand coverings, heat must be applied to the wrist in a manner that allows hands-free use. Further, the means for applying heat must be portable and of slight construction such that it does not significantly impair movement of the wrist region where it is applied. Prior attempts have been made to construct a portable thermal device which may be secured around the wrist of the user offering hands-free application of heat to the skin. However, many such devices contain metallic or plastic parts such as zippers, snaps or buckles which can conduct heat away from the intended region. Such devices also are often bulky significantly restricting movement of the wrist. Further, they are frequently of complicated construction and are not adaptable to the inexpensive heating elements with which those in need of such a device already are familiar.

Accordingly, there remains a need in the field of thermal regulation for a portable thermal device to be worn by a user which contains no plastic or metal parts and that does not significantly impede movement of the extremity being treated. Further, a device is needed into which a known, inexpensive heating element easily may be incorporated. The primary objective of this invention is to meet these needs.

SUMMARY OF THE INVENTION

Accordingly, it is an object of the present invention to provide a thermal device for maintaining the temperature of body extremities which is portable and of quality, inexpensive construction.

Another object of the present invention is to provide a thermal device for maintaining the temperature of body extremities which allows hands-free use.

Yet another object of the present invention is to provide a thermal device which is void of plastic or metal components.

It is a further object of the present invention to provide a thermal device for maintaining the temperature of body extremities into which a known heating element may be incorporated.

Still further, it is an object of the present invention to provide a thermal device for maintaining the temperature of body extremities which does not significantly impede movement of the portion of the body to which it is applied.

Accordingly, the present invention provides for a thermal device for maintaining the temperature of body extremities which includes a pocket adapted to receive a heating element and a strap attached to the pocket such that the device is adapted to encircle and be secured around a portion of the body. The pocket has a tri-fold configuration formed from a rear panel, a front panel, and an intermediate panel stacked atop one another, the intermediate panel being positioned between the front panel and the rear panel. Each of the three panels has a first and second vertical side edge.

The first vertical side edges of each panel are fixedly attached to one another as are the second vertical side edges of each panel. Each of the three panels also has a first and a second horizontal edge. The first horizontal edge of each of the front panel and the rear panel are fixedly attached to one another forming a first open space between the front panel and the intermediate panel, and the second horizontal edge of each of the rear panel and the intermediate panel are fixedly attached to one another forming a second open space therebetween. In operation, a heating element is inserted into an opening into the first open space and maneuvered around the first horizontal edge of the intermediate panel until it rests within the second open space of the pocket between the rear and intermediate panels. The device is then placed on the user with the pocket positioned on the interior surface of the wrist and secured in place with the strap allowing for hands-free use.

The invention also provides for a thermal device for maintaining the temperature of body extremities which includes a front panel, a rear panel, and an intermediate panel, and a strap attached to at least one of the panels and adapted to encircle and be secured around a portion of the body. Each panel has a first and a second horizontal edge. The intermediate panel is positioned between the front panel and the rear panel forming a first pocket between the front panel and the intermediate panel and a second pocket between the rear panel and the intermediate panel, each pocket having an opening therein and being adapted to receive a heating element. The first horizontal edges of each of the front panel and rear panel are at least partially attached and the first horizontal edges of each of the rear and intermediate panels are at least partially attached. In operation, a heating element is inserted in the opening into the first pocket and maneuvered around the first horizontal edge of the intermediate panel until it rests within the second pocket between the rear and intermediate panels. The device is then placed on the user with the pocket positioned on the interior surface of the wrist and secured in place with the strap allowing for hands-free use.

The invention further provides for a thermal device for maintaining the temperature of body extremities which includes a containing body having front, rear and intermediate bodies, and a strap attached to the containing body such that the device is adapted to encircle and be secured around a portion of the body. The intermediate body is positioned between the front and rear bodies forming a first open space between the front body and the intermediate body and a second open space between the intermediate body and the rear body. In the preferred embodiment, the front, rear and intermediate bodies are formed from a single, continuous length of material.

Additional objects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means, instrumentalities and combinations particularly pointed out in the appended claims.

BRIEF DESCRIPTION OF THE DRAWINGS

In the accompanying drawings which form a part of the specification and are to be read in conjunction therewith and in which like reference numerals are employed to indicate like parts in the various views.

DETAILED DESCRIPTION OF THE PREFERRED EMBODIMENT

Figure 1:
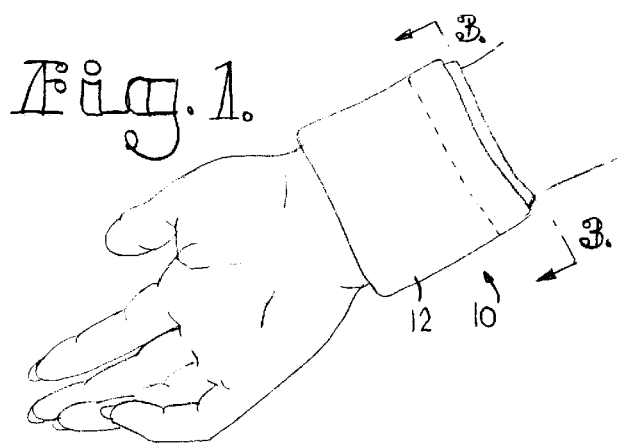
FIG. 1 is a perspective view of a thermal device positioned on the interior surface of the wrist of a user.

Referring to the drawings in greater detail, a thermal device designated generally by the numeral 10 is shown. Thermal device 10 has a fabric pocket 12 to which at least one strap 14 is suitably fastened. Pocket 12 is adapted to receive a heating element 16 and includes at least one opening for inserting and removing the heating element as more fully will be described below. Pocket 12 is of a tri-fold configuration which is formed from a front panel or body 18, a rear panel or body 20 and an intermediate panel or body 22. The panels are stacked atop one another with intermediate panel 22 positioned between front panel 18 and rear panel 20. The fabric which forms pocket 12 preferably includes an external surface which is of a texture comfortable to the touch since when in use it is in contact with the user's skin. Pocket 12 may be of any desired shape but is preferably an elongated rectangle of sufficient size for receiving a standard chemical hand warming device.

Each of front panel 18, rear panel 20 and intermediate panel 22, is preferably formed of an elongated rectangular shape. (For clarity of description, the elongated sides of the rectangle will be referred to as "horizontal" sides and the shorter sides will be referred to as "vertical" sides. Likewise, when speaking of the "top" and "bottom" edges, the "bottom" will be that which is closest to the hand when the preferred embodiment is viewed in operational placement on the interior of the wrist, the palm of the hand oriented toward the face. The "top" edge is the edge closest the body when the hand is in this orientation.) Each panel includes first and second vertical side edges. While each of the three panels is of approximately equal size, in the preferred embodiment, the first and second vertical side edges of intermediate panel 22 are of shorter vertical length than the first and second vertical side edges of rear panel 20. It is preferred that the first and second vertical side edges of intermediate panel 22 are about 25–50% shorter than the respective vertical side edges of rear panel 20. More preferably, the first and second vertical side edges of intermediate panel 22 are about 30% shorter than the vertical side edges of rear panel 20. In the preferred embodiment, the first vertical side edges of each of the three panels are fixedly attached to one another, at least partially, by any suitable means, for example, stitching, to form a first side junction. Likewise, the second vertical side edges of each of the three panels are fixedly attached to one another, at least partially, by any suitable means to form a second side junction. It is to be understood, however, that the scope of the present invention covers a device in which the vertical side edges of the panels are not fixedly attached.

Each of the front, rear and intermediate panels, 18, 20 and 22, also includes a first horizontal edge and a second horizontal edge. The first horizontal edges of each panel are aligned forming a first horizontal edge of the device and the second horizontal edges of each panel are aligned forming a second horizontal edge of the device. The second horizontal edge of front panel 18 and the first horizontal edge of intermediate panel 22 preferably include supplemental lengths of material which are folded under and secured by any suitable means, for example, stitching, to form edges which are smooth and free from imperfections which may snag or tear. The first horizontal edge of each of front panel 18 and rear panel 20 are fixedly attached to one another, at least partially, by stitching or the like to form a first open space between the front panel 18 and the intermediate panel 22. The second horizontal edge of each of rear panel 20 and intermediate panel 22 are fixedly attached to one another, at least partially, by stitching or the like to form a second open space therebetween.

This structure permits a device having two open spaces with the openings thereto at opposed edges of the device; the first open space having an opening positioned near the second horizontal edge of the device and the second open space having an opening positioned near the first horizontal edge of the device. However, as the opening to the second open space is enclosed between the front and rear panels 18 and 20, it is accessible only from inside of the first open space. Therefore, this structure permits a device having two open spaces in communication with one another housed within a single pocket 12, only one of the spaces having an opening which is exposed to the external environment. The structure thus described provides for secure placement of heating element 16 without the need for fastening means such as snaps, buckles, zippers or the like. If the vertical side edges of intermediate panel 22 are shorter than the corresponding vertical side edges of rear panel 20 as in the preferred embodiment, the opening into second open space is enlarged making access thereto simpler. In the preferred embodiment, the first horizontal edge corresponds with the bottom of the device and the second horizontal edge corresponds with the top of the device as viewed when the device is in operational placement on the wrist, hands at the user's sides. It is to be understood, however, that the device also may be used with the first horizontal edge corresponding with the top of the device and the second horizontal edge corresponding with the bottom of the device.

In the preferred embodiment, front panel 18, rear panel 20 and intermediate panel 22 are formed from a continuous length of material folded over itself to form the elongated, rectangularly-shaped panels necessary for the tri-fold configuration of pocket 12. While in the preferred embodiment the panels still are fixedly attached along their respective vertical side edges by way of stitching or the like, the continuous length of material eliminates the need for stitching together the first horizontal edges of front and rear panels 18 and 20 and the second horizontal edges of rear and intermediate panels 20 and 22. Supplemental lengths of material are folded under and stitched at each of the horizontal ends of the length of material. Once folded in the desired manner, these ends will represent the first horizontal edge of intermediate panel 22 and the second horizontal edge of front panel 18.

Strap 14 is attached to pocket 12 such that the device is adapted to encircle and be secured around a portion of the body. In a first embodiment (not shown), strap 14 may be formed of a continuous length of material which has elastic, resilient properties. One such suitable material is lycra. In this embodiment, strap 14 is formed of a rectangular shape having first and second horizontal edges and first and second vertical edges. In most instances, the vertical edges are of shorter overall length than the horizontal edges forming an elongated rectangular shape. However, it only is necessary that the horizontal edges be of a length suitable, when strap 14 is attached to pocket 12, for the device to encircle and be secured around the desired portion of the user's body.

The first and second vertical edges of the strap should approximate the length of the vertical side edges of front panel 18 and rear panel 20. In a preferred embodiment, the vertical edges of strap 14 are of lesser vertical length than the vertical side edges of the front and rear panels 18 and 20. The first vertical edge of the strap is attached to the pocket portion 12 at the first side junction and the second vertical edge is attached to the pocket portion 12 at the second side junction by any suitable means known in the art, such as stitching or the like. Each of the first and second vertical edges of the strap should be generally centered relative to the corresponding side junction such that strap 14 is approximately centered on pocket 12. This structure permits a device that may be stretched to slip over the hand of the user but returns to its original size and shape once in place on the wrist. The device is thus secured in place with the thermal device being held in appropriate position on the interior surface of the wrist of the user.

Figure 2:
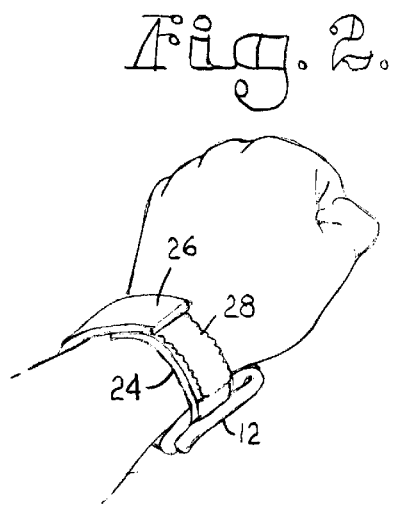
FIG. 2 is a perspective view of the thermal device in accordance with a preferred embodiment of the invention positioned on the wrist of a user as shown in FIG. 1, viewed from the back side of the wrist.
Figure 3:
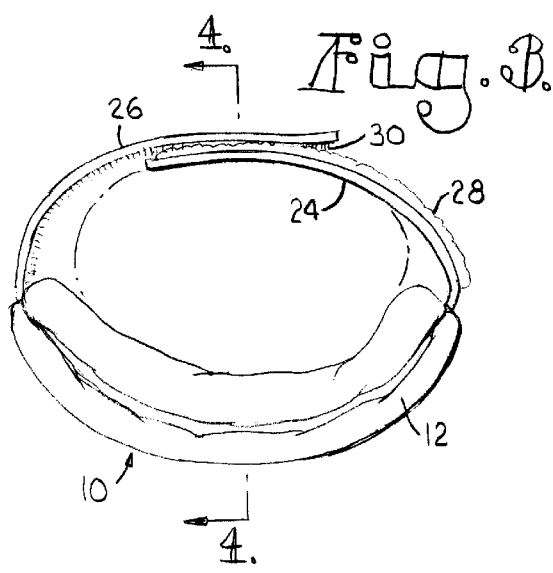
FIG. 3 is a top view of the thermal device taken along line 3—3 of FIG. 1 in the direction of the arrows.
Figure 4:
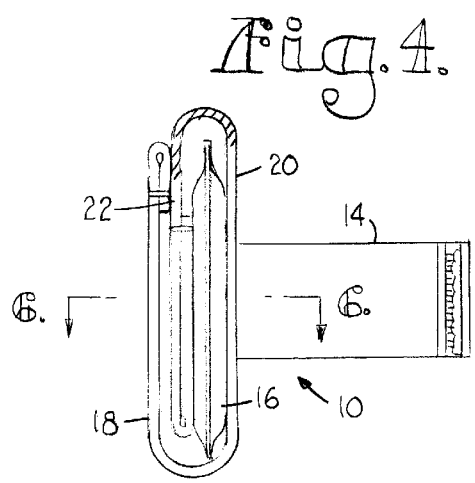
FIG. 4 is a cross-sectional view of the thermal device taken along line 4—4 of FIG. 3 in the direction of the arrows.
Figure 5:
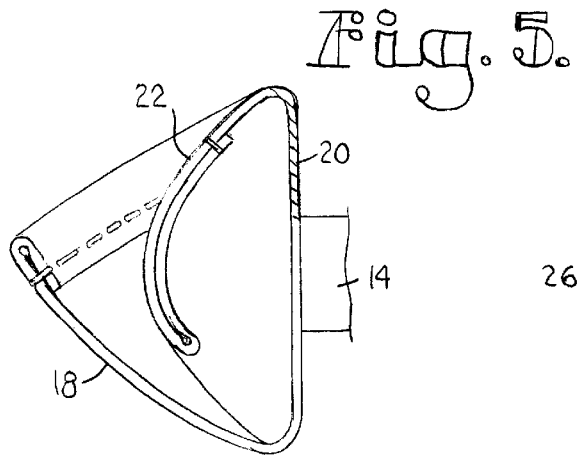
FIG. 5 is an exploded view of the thermal device illustrating the tri-fold configuration of the pocket.
Figure 6:
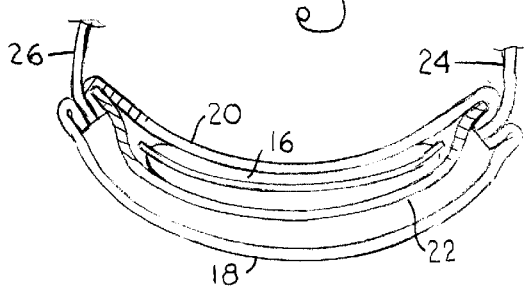
FIG. 6 is a cross-sectional view of the thermal device taken along line 6—6 of FIG. 4 in the direction of the arrows.

In an alternative embodiment, strap 14 may be formed of a first strap portion 24 and a second strap portion 26 as shown in FIGS. 2 and 3. Each portion of strap 14 is rectangular in shape with a first and a second horizontal edge and a first and second vertical edge. In most instances, the horizontal edges of each strap portion are longer than the corresponding vertical edges. However, it only is necessary that the combined length of the horizontal edges of first and second strap portions 24 and 26, when attached to pocket 12, be suitable for the device to encircle and be secured around the desired portion of the user's body. The vertical edges should approximate the length of the vertical edges of front and rear panels 18 and 20. In the preferred embodiment, the vertical edges of strap portions 24 and 26 are of a lesser vertical length than the vertical edges of the front and rear panels 18 and 20.

The first vertical edge of first strap portion 24 is fixedly attached to the first side junction of pocket 12 by any suitable means known in the art, such as stitching or the like. Likewise, the first vertical edge of second strap portion 26 is fixedly attached to the second side junction of pocket 12 by stitching or the like. It is preferred that strap portions 24, 26 be attached to the corresponding side junctions such that strap 14 is generally centered on pocket 12. First strap portion 24 is at least partially formed of a hook and loop material 28 and second strap portion 26 is at least partially formed of a complementary hook and loop material 30. Accordingly, the two strap portions cooperate to form an adjustable strap that is removably secured in place on the wrist of the user. The hook and loop material and its complement preferably are VELCRO (™). When the device is in position, first and second strap portions 24 and 26 are removably attached for holding the thermal device in place on the wrist of the user.

In operation, a heating element 16 is placed inside the pocket 12 of the thermal device 10 of the present invention. The heating element 16 is inserted into pocket 12 by moving it through the opening to first open space, maneuvering the heating element 16 around the first horizontal edge of intermediate panel 22 into second open space. When in place, the heating element 16 should be positioned such that it rests within the second open space between rear panel 20 and intermediate panel 22. Preferably, heating element 16 is inserted into pocket 12 prior to placement of the device on the wrist of the user. A well-known heating element which is suitable for use in the present invention is the Hand Warmer manufactured by GRABBER MYCOAL(™).

In the first embodiment, once heating element 16 is placed inside pocket 12, strap 14 is stretched and the device is placed over the hand of the user. Once the device is positioned around the user's wrist, the strap is released. The resilient properties of strap 14 will cause it to return generally to its initial size and shape prior to stretching thus holding the device securely in place. The rear panel 20 of pocket 12 is positioned on the interior surface of the user's wrist generally over the area under which the radial and ulnar arteries flow. If upon release of strap 14 pocket 12 is not so positioned, the device may be moved around the user's wrist until the desired positioning is achieved. If the device is not sufficiently tight to remain secure through the user's various movements, or for the user's comfort, clothing or the like may be placed over the device once it is placed in the desired position.

In the alternative embodiment, once heating element 16 is placed inside pocket 12, the hook-and-loop fasteners 28,30 on the first and second strap portions 24 and 26 are separated such that strap 14 is opened for placement around the user's wrist. The rear panel 20 of pocket 12 is placed on the interior surface of the user's wrist and the second vertical edges of each of first and second strap portions 24 and 26, are extended around to the back of the wrist and overlapped such that the hook-and-loop material 28 of first strap portion 24 and the complementary hook-and-loop material 30 of second strap portion 26 engage one another and secure the device in place. Pocket 12 is then moved around the user's wrist until it overlays the user's radial and ulnar arteries as in the first embodiment. If at any time device 10 needs to be tightened on the user's wrist, the first and second strap portions 24 and 26 are unhooked and then hooked again so that the overall length of strap 14 is shortened around the user's wrist. For the user's comfort, clothing or the like may be placed over the device once it is placed in the desired position.

In accordance with the above positioning of the preferred embodiment, heating element 16 is separated from the user's skin by only a single layer of material. To decrease the amount of heat applied to the skin, the device may be inverted on the wrist of the user such that the front panel rests on the interior of the wrist and the rear panel faces outwardly, i.e., toward the user when the palm of the hand is positioned toward the user's face. In this embodiment, two layers of material, the front panel and the intermediate panel, separate heating element 16 from the user's skin. To further decrease the amount of heat applied to the skin a sleeve or the like may be placed between the device and the skin of the user.

When utilized to maintain the temperature of the extremities, the thermal device of the present invention preferably is worn in pairs on opposing members of the body, for example, one on each wrist or one on each ankle, etc. The device, however, may be used singly, as desired. It is to be understood that the device is not limited to thermally regulating body extremities and may, in fact, be altered to any desired size and shape to regulate any desired portion of the anatomy. For example, as the kidneys are an area of significant blood flow, a torso-sized device may be made which applies heat to the lower back to minimize constriction of the vessels flowing to the kidneys. In the preferred embodiment, the thermal device is placed on the wrist of the user as illustrated in FIGS. 1 and 2.

Constructed and operated as previously described, this invention provides a portable, localized thermal device which minimizes constriction of the blood vessels in varying temperature conditions. The device is of quality, inexpensive construction and is void of plastic or metal components which may conduct heat away from the intended region of the user's anatomy. The device is of slight construction and thus does not significantly impede movement of the portion of the body to which it is applied. Further, the strap secures the device in place on the user allowing for hands-free use. The device also is adaptable to chemical heating elements which are known to those in the art.

From the foregoing, it will be seen that this invention is one well adapted to attain all the ends and objects hereinabove set forth together with other advantages which are obvious and which are inherent to the device.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

We claim:

1. A thermal device for maintaining the temperature of body extremities, comprising:

a pocket, said pocket adapted to receive a heating element and having a tri-fold configuration formed from a rear panel, a front panel, and an intermediate panel positioned atop one another, wherein said intermediate panel is positioned between said front panel and said rear panel, each said panel having a first and second vertical side edge, the first vertical side edges of each said panel being fixedly attached to one another forming a first side junction and the second vertical side edges of each said panel being fixedly attached to one another forming a second side junction, wherein each said panel includes a first horizontal edge and a second horizontal edge, the first horizontal edge of each of said front panel and said rear panel being fixedly attached forming a first open space between said front panel and said intermediate panel and the second horizontal edge of each of said rear panel and said intermediate panel being fixedly attached forming a second open space therebetween, and wherein said heating element is removably secured within said second open space solely by the tri-fold configuration formed from said rear panel, said front panel and said intermediate panel; and a strap attached to said pocket and being adapted to encircle and be secured around a portion of the human body.

2. A thermal device as specified in claim 1, wherein said front panel, said rear panel, and said intermediate panel are formed from a single, continuous length of material.

3. A thermal device as specified in claim 2, wherein said first and second vertical side edges of said intermediate panel are of a shorter vertical length than said first and second vertical side edges of said rear panel.

4. A thermal device as specified in claim 1, wherein said strap is formed from a resilient material.

5. A thermal device as specified in claim 1, wherein said strap is formed of a first portion at least partially formed of a hook and loop material and a second portion at least partially formed of a complementary hook and loop material, wherein said first and second portions cooperate to form an adjustable strap.

6. A thermal device for maintaining the temperature of body extremities, comprising:

a front panel having first and second horizontal edges;

a rear panel having first and second horizontal edges;

an intermediate panel having first and second horizontal edges, wherein said front, rear and intermediate panels are positioned atop one another, and wherein said intermediate panel is positioned between said front panel and said rear panel, wherein the first horizontal edge of each of said front panel and said rear panel are at least partially attached forming a first pocket between said front panel and said intermediate panel, said first pocket having a first opening therein, and wherein the second horizontal edge of each of said rear panel and said intermediate panel are at least partially attached forming a second pocket therebetween, said second pocket having a second opening therein, wherein the device is adapted to receive a heating element inserted through said opening in said first pocket, maneuvered around said first horizontal edge of said intermediate panel and subsequently inserted through said opening in said second pocket, and wherein said heating element is adapted to be removably secured within said solely by the positioning of said rear panel, said front panel and said intermediate panel atop one another; and a strap attached to at least one of said panels and being adapted to encircle and be secured around a portion of the human body.

7. A thermal device as specified in claim 6, wherein said front panel, said rear panel, and said intermediate panel are formed from a single, continuous length of material.

8. A thermal device as specified in claim 7, wherein each of said front, rear and intermediate panels further comprises:

a first vertical side edge; and a second vertical side edge, wherein the first vertical side edges of each said panel are at least partially attached to one another, and wherein the second vertical side edges of each said panel are at least partially attached to one another.

9. A thermal device as specified in claim 8, wherein said first and second vertical side edges of said intermediate panel are of a shorter vertical length than said first and second vertical side edges of said rear panel.

10. A thermal device as specified in claim 6, wherein said strap is formed from a resilient material.

11. A thermal device as specified in claim 6, wherein said strap is formed of a first portion, wherein said first portion is at least partially formed of a hook and loop material and a second portion, wherein said second portion is at least partially formed of a complementary hook and loop material, and wherein said first and second portions cooperate to form an adjustable strap.

12. A thermal device for maintaining the temperature of body extremities, comprising:

a containing body having a front, a rear, and an intermediate body positioned atop one another, wherein said intermediate body is positioned between said front body and said rear body forming a first open space between said front body and said intermediate body and a second open space between said intermediate body and said rear body, a heating element removably secured within said second open space solely by said rear body, said front body and said intermediate body; and a strap attached to said containing body and being adapted to encircle and be secured around a portion of the human body.

13. A thermal device as specified in claim 12, wherein said front, rear and intermediate bodies are formed from a single, continuous length of material.

* * * * *